(12) United States Patent
Greenhalgh et al.

(10) Patent No.: US 8,252,054 B2
(45) Date of Patent: Aug. 28, 2012

(54) EXPANDABLE SUPPORT DEVICE AND METHOD OF USE

(75) Inventors: E. Skott Greenhalgh, Lower Gwynedd, PA (US); John-Paul Romano, Chalfont, PA (US)

(73) Assignee: Stout Medical Group, L.P., Perkasie, PA (US)

( * ) Notice: Subject to any disclaimer, the term of this patent is extended or adjusted under 35 U.S.C. 154(b) by 117 days.

(21) Appl. No.: 12/684,825

(22) Filed: Jan. 8, 2010

(65) Prior Publication Data
US 2010/0179657 A1    Jul. 15, 2010

Related U.S. Application Data

(60) Provisional application No. 61/205,081, filed on Jan. 14, 2009.

(51) Int. Cl.
*A61F 2/44* (2006.01)
(52) U.S. Cl. .................. 623/17.11; 623/17.16
(58) Field of Classification Search .......... 606/246–249, 606/279; 623/17.11–17.16
See application file for complete search history.

(56) References Cited

U.S. PATENT DOCUMENTS

| | | | |
|---|---|---|---|
| 5,514,180 | A | 5/1996 | Heggeness et al. |
| 6,176,881 | B1 * | 1/2001 | Schar et al. ................ 623/17.11 |
| 6,193,756 | B1 | 2/2001 | Studer et al. |
| 6,200,348 | B1 | 3/2001 | Biedermann et al. |
| 6,524,341 | B2 | 2/2003 | Lang et al. |
| 6,616,695 | B1 | 9/2003 | Crozet et al. |
| 6,730,088 | B2 | 5/2004 | Yeh |
| 6,860,525 | B2 | 3/2005 | Parks |
| 6,866,682 | B1 | 3/2005 | An et al. |
| 6,902,579 | B2 | 6/2005 | Harms et al. |
| 7,056,343 | B2 | 6/2006 | Schäfer et al. |
| 7,156,874 | B2 | 1/2007 | Paponneau et al. |
| 7,311,733 | B2 | 12/2007 | Metz-Stavenhagen |
| 7,458,988 | B2 | 12/2008 | Trieu et al. |
| 7,544,208 | B1 | 6/2009 | Mueller et al. |
| 2005/0096744 | A1 | 5/2005 | Trieu et al. |
| 2005/0228501 | A1 | 10/2005 | Miller et al. |
| 2006/0058879 | A1 | 3/2006 | Metz-Stavenhagen |
| 2006/0200244 | A1 | 9/2006 | Assaker |
| 2006/0241762 | A1 | 10/2006 | Kraus |
| 2007/0250171 | A1 | 10/2007 | Bonin, Jr. |

(Continued)

FOREIGN PATENT DOCUMENTS

EP    1080703    3/2001
(Continued)

OTHER PUBLICATIONS

Franklin et al., "Uptake of Tetracycline by Aortic Aneurysm Wall and Its Effect on Inflammation and Proteolysis," *Brit. J. Surger*, 86(6):771-775.

(Continued)

*Primary Examiner* — Eduardo C Robert
*Assistant Examiner* — Christina Negrelli
(74) *Attorney, Agent, or Firm* — Levine Bagade Han LLP

(57) ABSTRACT

An expandable support device and methods of using the same are disclosed herein. The expandable support device can expand longitudinally. The expandable support device can be deployed in a bone, such as a vertebra, for example to repair a compression fraction or replacement of removed tissue, such as a vertebra or vertebral body. The expandable support device can be deployed into or in place of all or part of an intervertebral disc.

19 Claims, 12 Drawing Sheets

U.S. PATENT DOCUMENTS

| | | |
|---|---|---|
| 2007/0255408 A1 | 11/2007 | Castleman et al. |
| 2007/0255409 A1 | 11/2007 | Dickson et al. |
| 2007/0255421 A1 | 11/2007 | Dickson |
| 2008/0103601 A1 | 5/2008 | Biro et al. |
| 2008/0243254 A1 | 10/2008 | Butler |
| 2008/0262501 A1 | 10/2008 | Chen et al. |
| 2008/0288071 A1 | 11/2008 | Biyani et al. |
| 2009/0138083 A1 | 5/2009 | Biyani |
| 2009/0138089 A1 | 5/2009 | Doubler et al. |
| 2009/0164017 A1 | 6/2009 | Sommerich et al. |

FOREIGN PATENT DOCUMENTS

| | | |
|---|---|---|
| JP | 62-164458 A | 7/1987 |
| WO | WO 98/46173 | 10/1998 |
| WO | WO 02/45625 | 6/2002 |
| WO | WO 03/082363 | 10/2003 |
| WO | WO 2004/100837 | 11/2004 |
| WO | WO 2005/055887 | 6/2005 |

OTHER PUBLICATIONS

Pyo et at., "Targeted Gene Disruption of Matrix Metalloproteinase-9 (Gelatinase B) Suppresses Development of Experimental Abdominal Aortic Aneurysms." *J. Clinical Investigation*, 105(11):1641-1649.

Tambiah et al., "Provocation of Experimental Aortic Inflammation Mediators and Chlamydia Pneumoniae," *Brit., J. Surgery*, 88(7):935-940.

Walton et al., "Inhibition of Prostoglandin E2 Synthesis in Abdominal Aortic Aneurysms," *Circulation*, 48-54, Jul. 6, 1999.

Xu et al., "Sp1 Increases Expression of Cyclooxygenase-2 Hypoxic Vascular Endothelium," *J. Biological Chemistr*, 275(32):24583-24589.

* cited by examiner

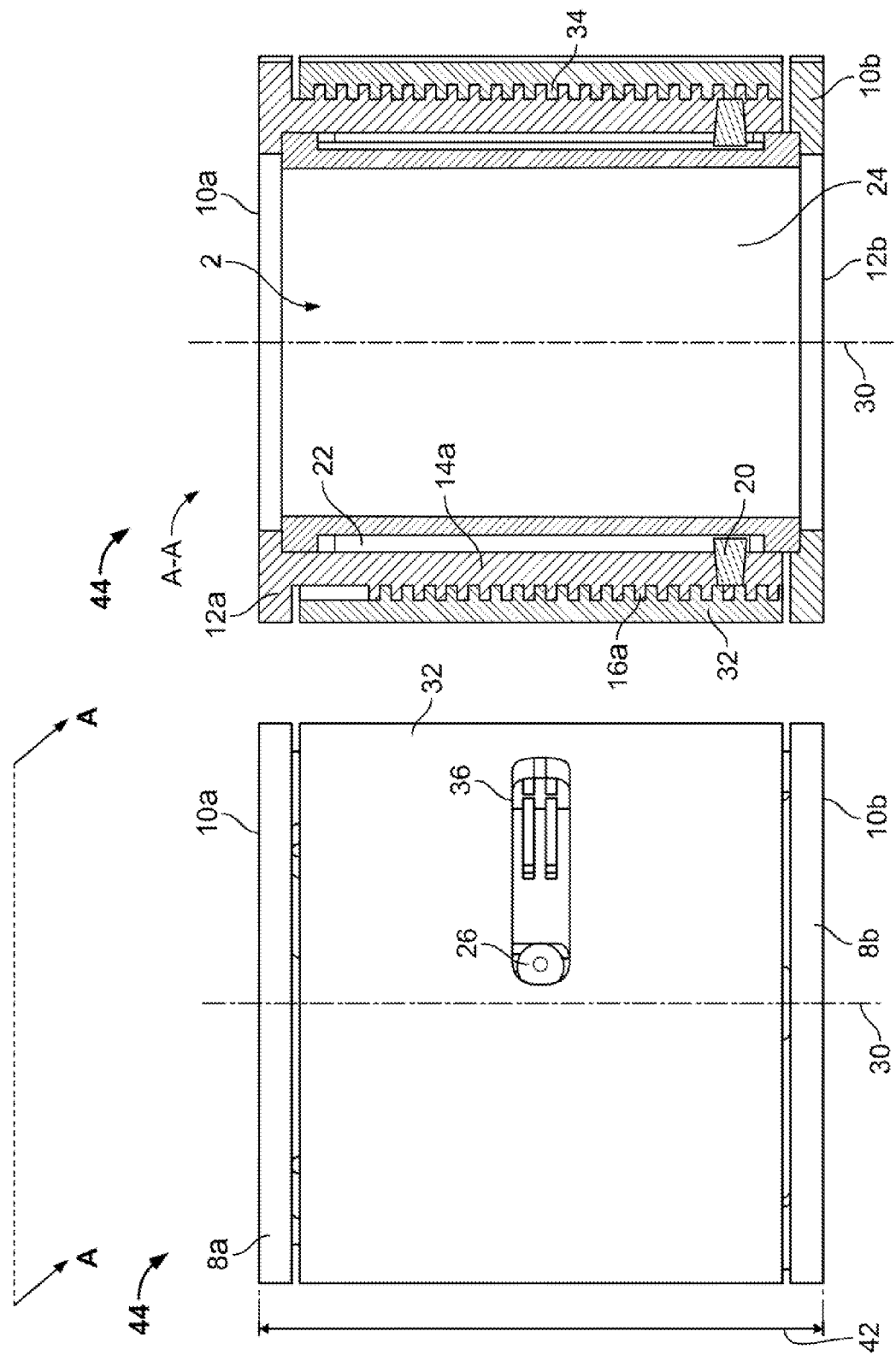

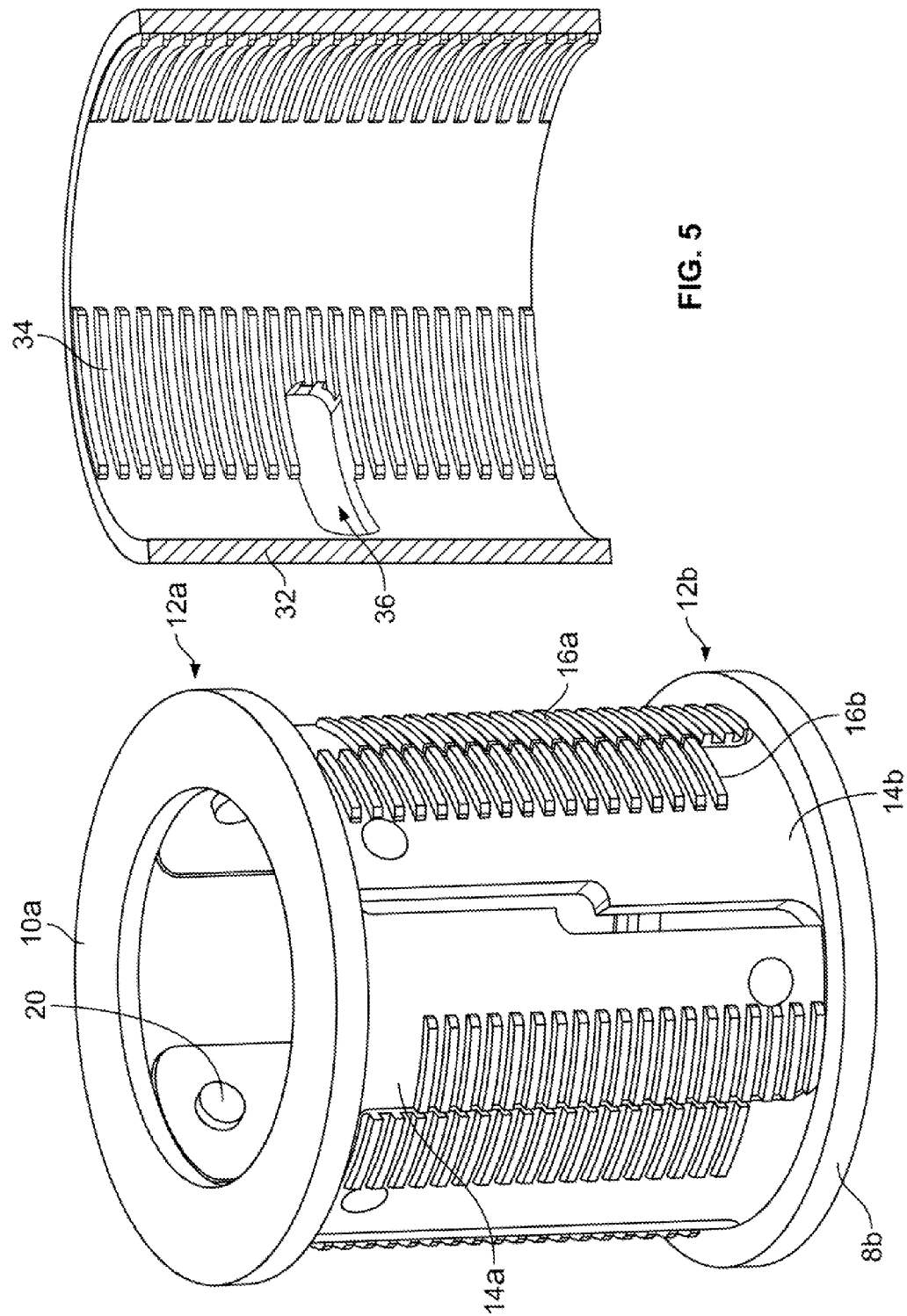

NOT INVENTION

NOT INVENTION

EXPANDABLE SUPPORT DEVICE AND METHOD OF USE

CROSS-REFERENCE TO RELATED APPLICATIONS

This application claims the benefit of U.S. Provisional Application No. 61/205,081, filed Jan. 14, 2009, which is incorporated by reference herein in its entirety.

BACKGROUND OF THE INVENTION

1. Field of the Invention

This invention relates to expandable support devices for biological implantation and methods of using the same. More specifically, the expandable support devices can be used to treat vertebral pathologies.

2. Description of Related Art

Corpectomy occurs when vertebral bodies of one or more vertebrae are removed. Corpectomy is often performed due to trauma, damage to the bone from cancer, to treat pain (e.g., due to nerve compression, such as in spinal stenosis), spinal deformities, and compression fractures. Corpectomy procedures can also be performed to spinal cord compression caused by bone spur (osteophyte) growth.

Corpectomy is often performed with a discectomy, a procedure in which the intra-vertebral disc is removed. The discs on both sides of the vertebral body can be removed with the vertebral body. Corpectomy procedures can result in decompressing the spinal cord and nerves resulting in reduced or eliminated symptoms from vertebral pathologies, such as reduced pain.

Once the vertebral bodies are removed, structural, mechanical support is needed to replace the mechanical function of the vertebral bodies. Fixation between the vertebrae adjacent to the corpectomy site is often performed. Access to the target site where the corpectomy was performed is desired to be limited to minimize damage to surrounding tissue.

Existing fixation devices include longitudinally expandable devices that can be placed between in the location of the removed vertebral bodies between the remaining vertebral bodies. The devices can contact the vertebral bodies on opposite sides of the corpectomy site. Among other short comings, these devices often have a limited expansion ratio, inconvenient locking features, and/or need complicated tooling for deployment and repositioning or removal.

Accordingly, a structural support device is desired that can fulfill the structural demands of the removed vertebral bodies while still being easy to deploy in a small space. A need exists for a structural support device for a corpectomy site that can expand to a large longitudinal expansion ratio, have a convenient and easy-to-use locking feature, and does not necessitate the use of complicated tooling.

SUMMARY OF THE INVENTION

Devices for providing support for biological tissue, for example in corpectomy procedures, to repair spinal compression fractures, and methods of using the same are disclosed.

For example, an orthopedic mechanical support device having a longitudinal axis is disclosed. The device has a first hollow member, a second hollow member, a rotationally limiting element, and a first longitudinally extending member.

The first hollow member, such as an outer cylinder, can have a screw slot therethrough. The screw slot is defined by a first stop at a first terminal end of the screw slot and a second stop at the second terminal end of the screw slot.

The second hollow member, such as an inner cylinder, can be positioned radially inside of the first hollow member. The second hollow member can be configured to rotate with respect to the first hollow member.

A rotationally limiting element, such as a lock screw, can be radially extending from the second hollow member. The rotationally limiting element can be received by the screw slot. The rotationally limiting element and screw slot can be configured to abut each other at the first stop to limit rotation of the second hollow member with respect to the first hollow member in a first direction. The rotationally limiting element and the screw slot can be configured to abut at the second stop to limit the rotation of the second hollow member with respect to the second hollow member in the second direction.

The first longitudinally extending member, such as a first end piece, can be configured to longitudinally slide with respect to the first hollow member in a first direction away from the first hollow member when the first hollow member is in a first, unlocked, rotational position with respect to the first longitudinally extending member. The first longitudinally extending member can be configured to be longitudinally fixed with respect to the first hollow member when the first hollow member is in a second, locked, rotational position with respect to the first longitudinally extending member. The first longitudinally extending member can be configured to be longitudinally slidable along and rotationally fixed to the second hollow member.

The device can also have a second longitudinally extending member, such as a second end piece. The second end piece can be longitudinally lockable and unlockable by rotating the first hollow member, as described above for the first longitudinally extending member, except the second longitudinally extending member can extend in the direction opposite to the direction the first longitudinally extending member extends.

The first longitudinally extending member can have a first end face, a first extension can longitudinally extending from the first end face, and a second extension longitudinally extending from the first end face. A first gap can be formed between the first extension and the second extension.

The second longitudinally extending member can have a second end face, a third extension longitudinally extending from the second end face, and a fourth extension longitudinally extending from the second end face. A second gap can be formed between the third extension and the fourth extension. Because the extending members will longitudinally overlap when expanded away from and contracted to the hollow members, the first extension can be configured to longitudinally slide within the first gap. The third extension is configured to longitudinally slide within the second gap.

The second hollow member can have a longitudinal guide, such as a guide slot or rail. The first extension can have a guide interface, such as a guide peg or groove, configured to interface with the guide. The guide interface can be longitudinally slidable along the guide and rotationally fixed with respect to the guide.

The first longitudinally extending member can have a radially outwardly extending locking feature, such as a first end piece tooth. The first hollow member can have a radially inwardly extending locking feature, such as an outer cylinder tooth. The outwardly extending locking feature can interference fit in the longitudinal direction against the inwardly extending locking feature when the first hollow member is in the second, locked, rotational position with respect to the second hollow member.

The screw slot can be oriented in a plane perpendicular to the longitudinal axis. The first hollow member and the second hollow member can be substantially cylindrical. The first end face can be closed, or open or hollow, for example to enable the introduction of filler into a center channel defined by the hollow members. Filler can also be inserted through gaps or end piece slots between the end piece extensions.

Also described herein is an orthopedic mechanical support device having a longitudinal axis that can have a first hollow member, a second hollow member, a first longitudinally extending member, and a second longitudinally extending member.

The first hollow member can have an inner diameter wall, for example facing the center channel, and a first hollow member locking feature, such as an outer cylinder tooth. The first hollow member locking feature can extend radially inwardly from the inner diameter wall.

The second hollow member can be radially inside of the first hollow member. The second hollow member can be rotatable with respect to the first hollow member. The second hollow member can have a first guide and a second guide, such as first and second longitudinally oriented guide slots.

The first longitudinally extending member can have a first radially outwardly extending locking feature, such as a first end piece tooth, and a first radially inwardly extending guide interface, such as a guide peg.

The second longitudinally extending member can have a second radially outwardly extending locking feature, such as a second end piece tooth, and a second radially inwardly extending guide interface, such as a guide peg.

The first guide interface can interface with the first guide to limit the rotation between the second hollow member and the first longitudinally extending member. The first guide interface can interface with the first guide to allow and limit longitudinal movement between the second hollow member and the first longitudinally extending member.

The second guide interface can interface with the second guide to limit the rotation between the second hollow member and the second longitudinally extending member. The second guide interfaces with the second guide to allow and limit longitudinal movement between the second hollow member and the second longitudinally extending member.

The first hollow member can have a second hollow member locking feature, such as an outer cylinder tooth extending inwardly in a different column than the first hollow member locking feature. A locking gap can be defined between the first hollow member locking feature and the second hollow member locking feature.

The width of the first radially outwardly extending locking feature and the second radially outwardly extending locking feature can together be less than or equal to the width of the locking gap.

The width of the first radially outwardly extending locking feature and the second radially outwardly extending locking feature can each be less than the width of the hollow member locking feature.

A rotationally limiting element, such as the lock screw, can extend from the second hollow member through the first hollow member. The rotation of the first hollow member with respect to the first longitudinally extending member and the second longitudinally extending member can be limited by the rotationally limiting element interference fitting against the first hollow member, for example against the first and second stops of the screw slot of the outer cylinder.

A method for mechanically supporting an orthopedic site is also disclosed. The method can include inserting a longitudinally expandable device into the orthopedic site. The support device can have a longitudinal axis. The device can have a first hollow member, a second hollow member radially inside of the first hollow member, and a first longitudinally extending member slidably received by the first hollow member. The method can also include longitudinally extending the first longitudinally extending member away from the first hollow member. The method can also include longitudinally fixing the first longitudinally extending member to the first hollow member. Longitudinally fixing can include rotating the first hollow member with respect to the first and/or second longitudinally extending member.

The support device can include a second longitudinally extending member slidably received by the second hollow member. The method can include longitudinally extending the second longitudinally extending member from the first hollow member in a direction opposite to a direction of the extension of the first longitudinally extending member.

Rotating the first hollow member can include rotating the first hollow member until the first hollow member interference fits against a feature of the second hollow member.

During the method, longitudinally extending the first longitudinally extending member can include longitudinally sliding a guide interface, such as a guide peg, on the first longitudinally extending member along a guide, such as the guide slot, on the second hollow member. The method can include rotationally restricting the first longitudinally extending member with respect to the second hollow member, for example by rotationally constraining the guide peg within the guide slot.

The method can include removing a vertebral body from the orthopedic site before inserting the expandable device into the orthopedic site. The method can also include partially or completely filling the device with a filler, described herein, before, during or after the device has been inserted at the target site and longitudinally expanded.

BRIEF DESCRIPTION OF THE DRAWINGS

FIG. 2a is a side view of a variation of the expandable support device in a longitudinally contracted configuration.

FIG. 2b illustrates a variation of cross-section A-A of FIG. 2a.

FIG. 3b illustrates a variation of cross-section B-B of FIG. 3a.

FIG. 4 illustrates a variation of a first end piece adjacent to a second end piece.

FIG. 5 is a variation of a cross-section of the outer cylinder.

DETAILED DESCRIPTION

Figure 1:
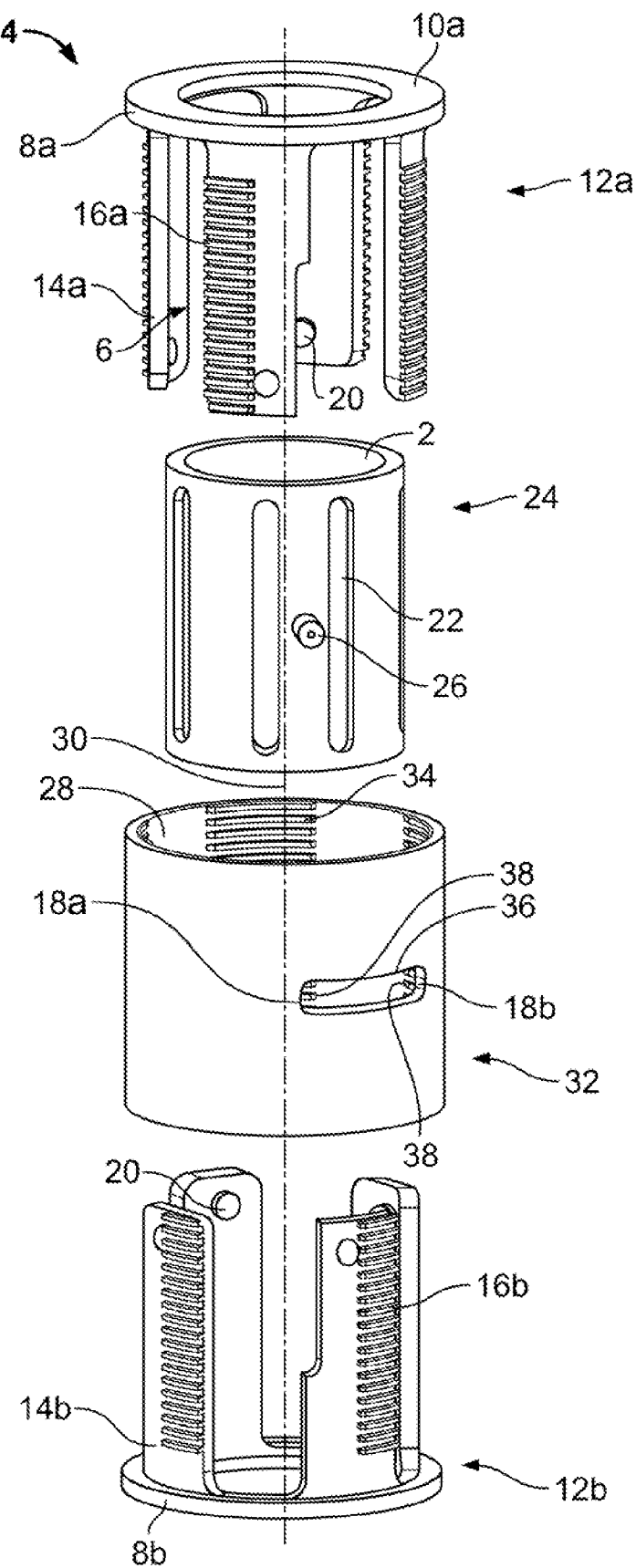
FIG. 1 is an exploded view of a variation of the expandable support device.

FIG. 1 illustrates that the expandable support device 4 that can be used to implant into a corpectomy site. One or more adjacent vertebral bodies 66 and one or both surrounding vertebral discs—as well as the vertebral discs between the removed vertebral bodies 66—can be removed from a target site 68. The expandable support device 4 can then be inserted into the target site 68 and expanded to provide mechanical support in the spine 62 between the remaining vertebral bodies 66.

The expandable support device 4 can have an outer cylinder 32, an inner cylinder 24, a first end piece 12a and a second end piece 12b. The expandable support device 4 can be expanded and can mechanically, structurally support orthopedic structures in vivo, whether those orthopedic structures are the aforementioned vertebrae 64, other bones, or soft tissue.

The first end piece 12a and second end piece 12b can be substantially identical or different from each other in shape and structure. The first end piece 12a can be symmetric or a mirror-image of the second end piece 12b. The first 12a and second 12b end pieces can have terminal first 8a and second 8b ends, respectively. The ends can have end faces. The end faces can be smooth or textured. The end faces can be textured with knurling, spikes, ridges, bumps, or combinations thereof. A first end face 10a can be textured with a first texture and the second end face 10b can be smooth or textured with a second texture that can be the same or different from the first texture. The end faces can be configured to abut or dig into adjacent tissue (e.g., bone) during implantation. Either or both end faces can be made from or lined with a matrix to encourage tissue ingrowth into the end face.

The end pieces can have one or more end piece extensions or legs extending from the respective end faces longitudinally inward toward the longitudinal center of the expandable support device 4. The extensions can have one or more radially outward-facing end piece teeth. The end piece teeth can be configured in a longitudinal column parallel with the longitudinal axis 30 on each extension. The end piece teeth can be oriented in transverse planes, perpendicular to the longitudinal axis 30 and along an angular path at a constant radius with respect to the longitudinal axis 30. Each end piece tooth can extend across half (as shown) or substantially all of the radially outer surface of the extension.

One, two or all of the extensions can have radially inwardly-facing guide pegs 20. The guide pegs 20 can be at or near the longitudinally terminal ends of the extensions away from the respective end face.

End piece slots 6 can be formed by open areas between the extensions.

The inner cylinder 24 can form a center channel 2. The inner cylinder 24 can have longitudinal guide slots 22 on the radially outer surface of the inner cylinder 24. The guide pegs 20 can be configured to interface with, or receive, the guide pegs 20. The guide slots 22 can be configured to longitudinally slidably attach to the guide pegs 20. The guide slots 22 can constrain the guide pegs 20 to prevent the end pieces (and guide pegs 20) from rotating with respect to the inner cylinder 24.

During use, filler can be inserted through the end piece slots 6 and into the center channel 2 before during or after insertion of the device 4 into the target site 68 and/or extension of the device 4. The filler can be chunks of morselized bone, powder (e.g., BMP), liquid (e.g., PMMA), all of which are listed and for which examples are given below, or combinations thereof.

The inner cylinder 24 can have one or more a radially outwardly extending lock screws 26. The lock screws 26 can have heads at the radially outermost terminal end of the lock screw 26. The heads of the lock screws 26 can be wider than the shafts of the lock screws 26. The lock screws 26 can be spring-loaded, clips, or combinations thereof.

The outer radius of the inner cylinder 24 can be smaller than the inner radius of the end piece extensions.

The outer cylinder 32 can have a screw slot 36 configured to slidably receive the lock screw 26. The outer cylinder 32 can have an inner radius that is larger than the outer radius of the end piece extensions.

The screw slot 36 can have a first stop 18a at a first terminal end of the screw slot 36. The screw slot 36 can have a second stop 18b at a second terminal end of the screw slot 36. The first 18a and second 18b stops can abut and interference fit against the lock screw 26 shaft when the outer cylinder 32 and inner cylinder 24 are rotated with respect to each other to the respective limits of rotation. The angular limit of rotation of the outer cylinder 32 with respect to the inner cylinder 24 can be defined by and identical to the screw slot angle 38. The screw slot angle 38 can be an angle measured from the longitudinal axis 30 between the first stop 18a and the second stop 18b.

The outer cylinder 32 can have columns of radially inwardly-facing outer cylinder teeth 34. The outer cylinder teeth 34 can be configured in longitudinal columns parallel with the longitudinal axis 30. The outer cylinder teeth 34 can be oriented in transverse planes, perpendicular to the longitudinal axis 30 and along an angular path at a constant radius with respect to the longitudinal axis 30. The outer cylinder teeth 34 can have be spaced so the toothless areas of the inner surface of the outer cylinder 32 can define a locking gap 28 between adjacent columns of outer cylinder teeth 34. The locking gaps 28 can be are at least as wide as the width of the end piece teeth. The end piece teeth can be narrower than the outer cylinder teeth 34.

The end piece teeth can slide between the outer cylinder teeth 34 when the outer cylinder 32 is rotated appropriately with respect to the end pieces. When the guide pegs 20 are engaged in the guide slots 22, the end pieces and inner cylinder 24 can rotate as a single unit with respect to the outer cylinder 32. The screw slot 36 and screw can be configured so that the end piece teeth do not longitudinally interfere with the outer cylinder teeth 34 (i.e., an unlocked configuration) when the screw is at one end of the screw slot 36. For example, this unlocked configuration can permit the end pieces to longitudinally translate (i.e., expand and contract) with respect to the outer cylinder 32 and the opposite end piece.

The screw slot 36 and screw can be configured so that the end piece teeth longitudinally interfere with the outer cylinder teeth 34 (i.e., a locked configuration) when the screw is at the opposite end of the screw slot 36 from the unlocked configuration. For example, this locked configuration can create an interference fit between the end piece teeth and the outer cylinder teeth 34, for example, substantially preventing the end pieces from longitudinally translating (i.e., expand and contract) with respect to the outer cylinder 32 and the opposite end piece.

The device 4 can have snaps or threads on the end pieces, for example to engage the vertebral body 66 end plates. The end pieces can be smooth or rough (e.g., with texturing or teeth). The end pieces can have angles relative to the longitudinal axis 30 of the cylinders and/or the other end piece. The devices end pieces can have teeth or angle without the snap on pieces.

The end pieces can have four extensions, as shown, or more or less extensions. The end piece teeth can be next to each other, as shown, or can be in the center of each column. The ratio of the outer surface area of the end piece extensions covered by teeth to non-tooth surface area can be about 50%.

Figure 3A:
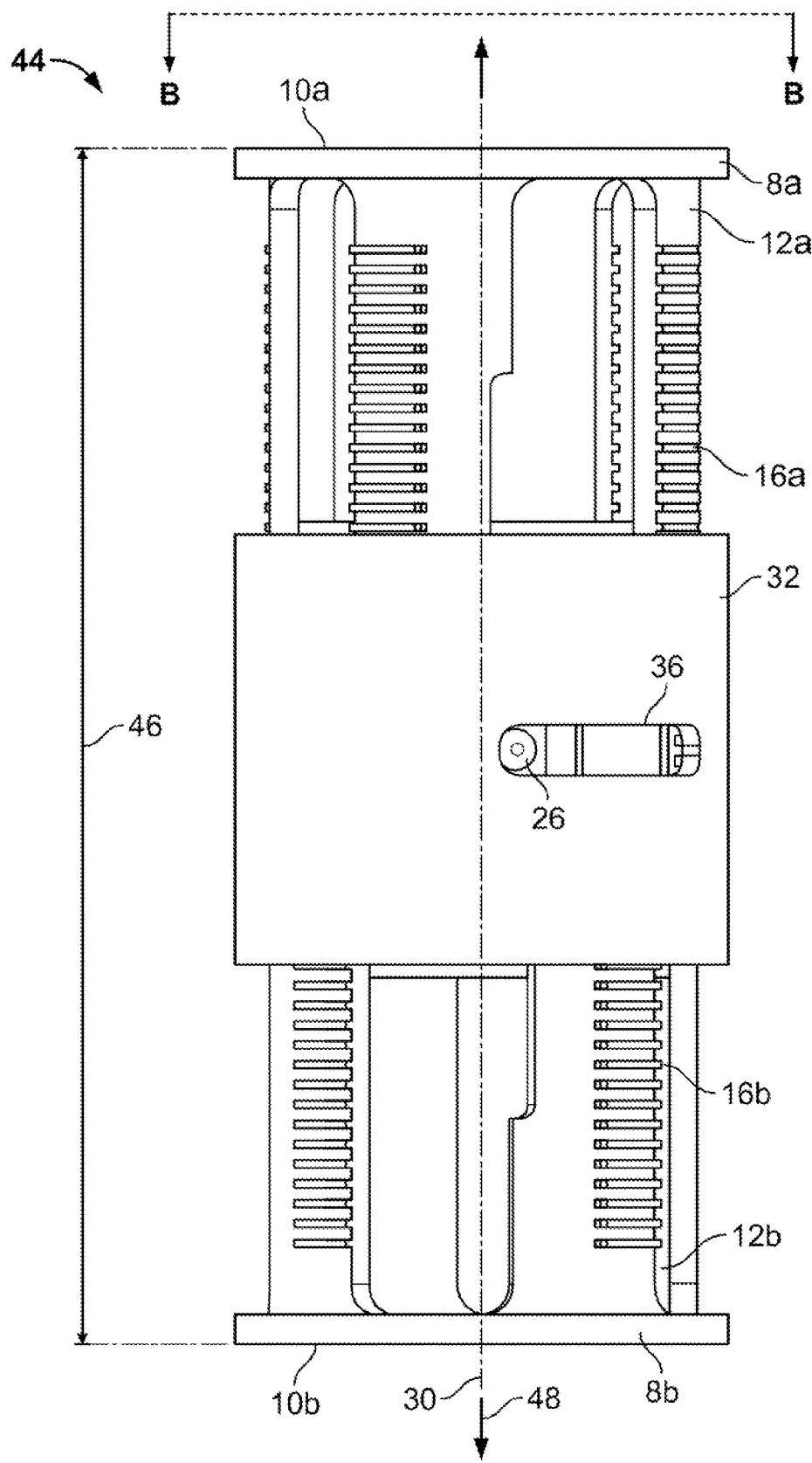
FIG. 3a is a side view of the device of FIG. 3a in a longitudinally expanded configuration.
Figure 3B:
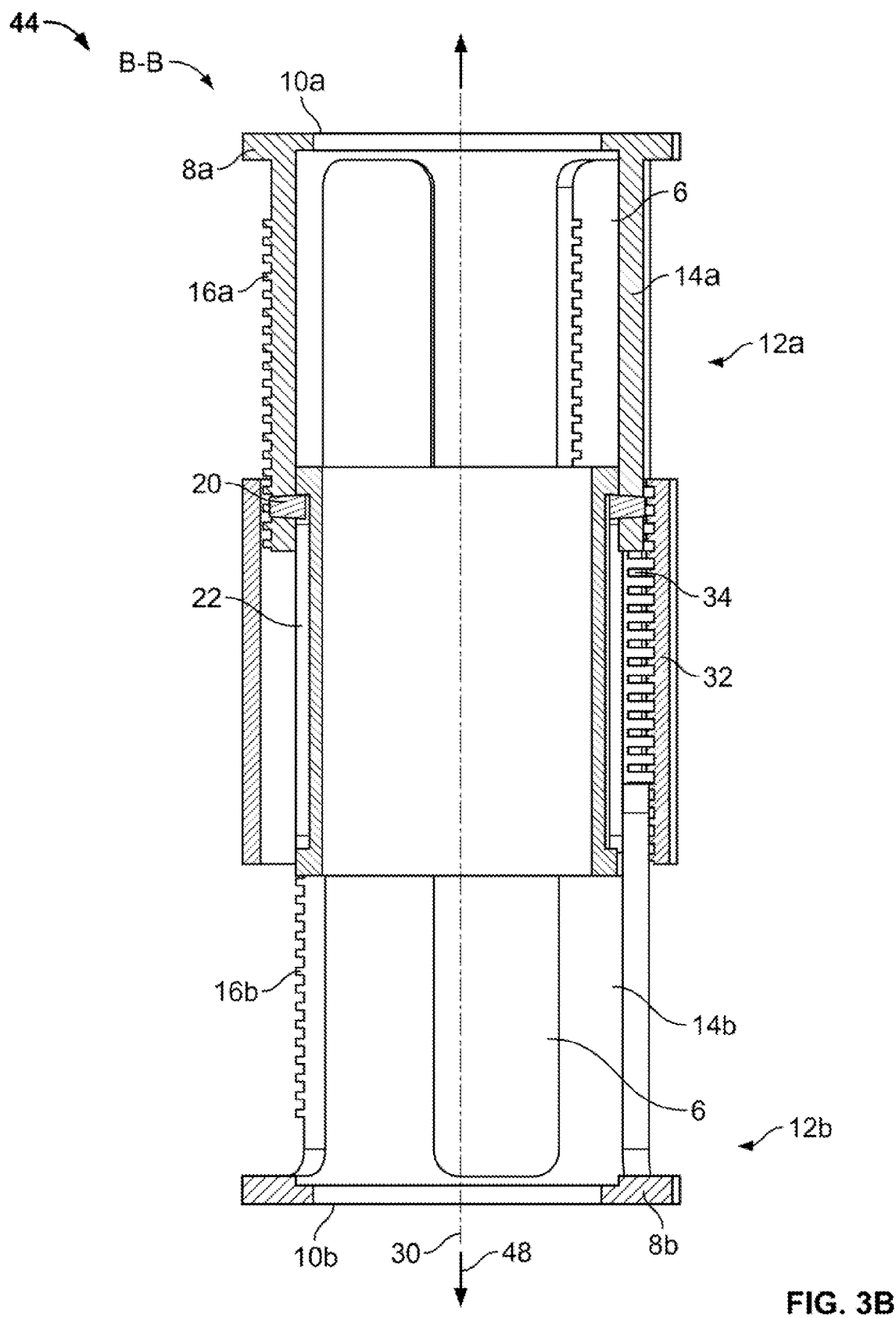
Figure 3C:
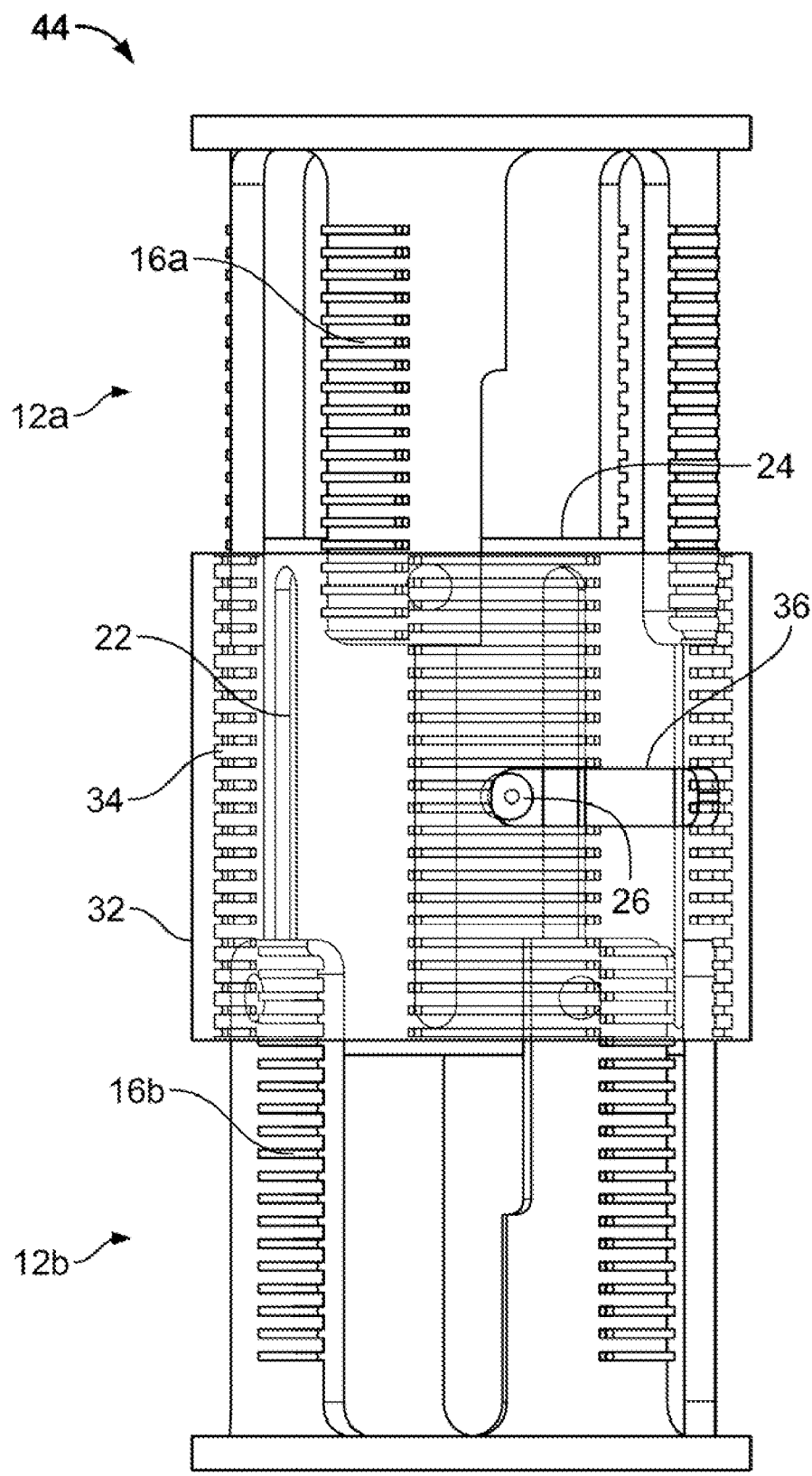
FIGS. 3c and 3d are partially see-through views of a variation of the device of FIG. 2b in a longitudinally expanded configuration in unlocked and locked configurations respectively.
Figure 3D:
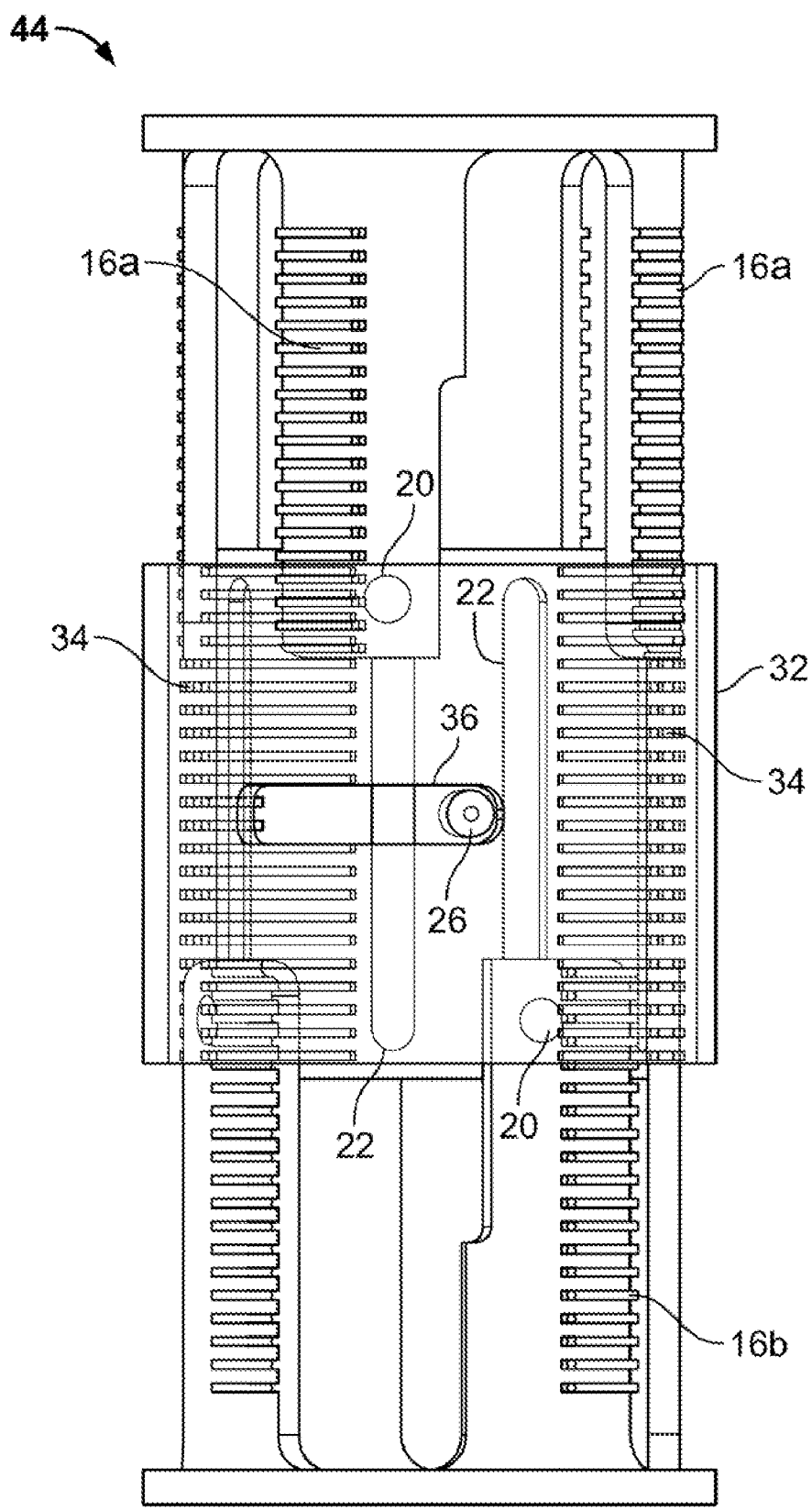
Figure 6:
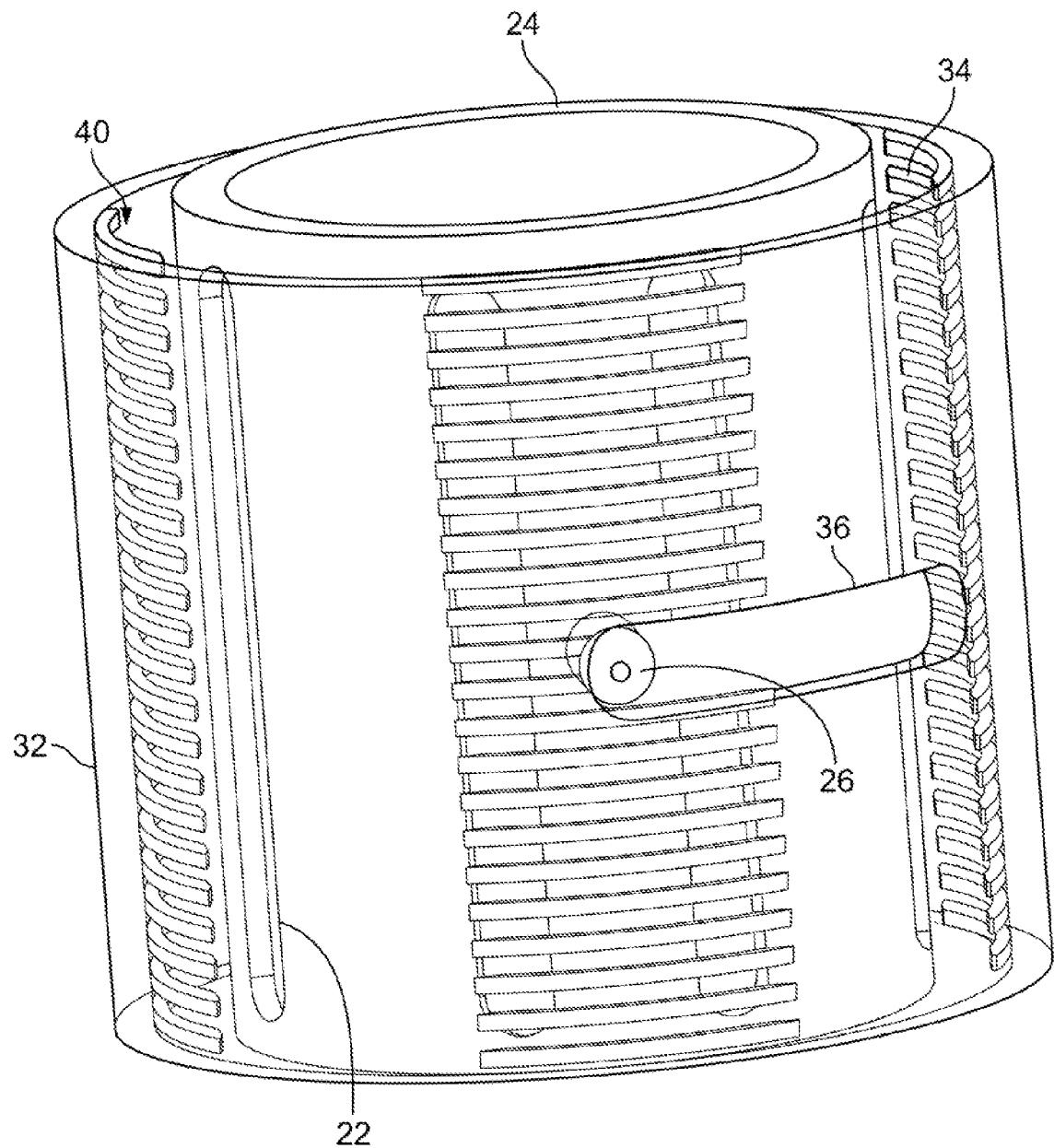
FIG. 6 illustrates a variation of the inner cylinder with a partial see-through view of the outer cylinder.

FIG. 2a illustrates that the contracted length 42 can be about 1 in. FIG. 3a illustrates that the expanded length 46 can be about 2.4 in.

The device can have a device first end 8a and a device second end 8b. The terminal ends, such as the end faces can have anchors. The anchors can be rounded or sharpened. The end anchors can have a rough or smooth texture. The end anchors can be coated with a material different or the same as the remainder of the device. The end anchors can be configured to seat in and/or affix to and/or heal to bone.

Figure 7C:
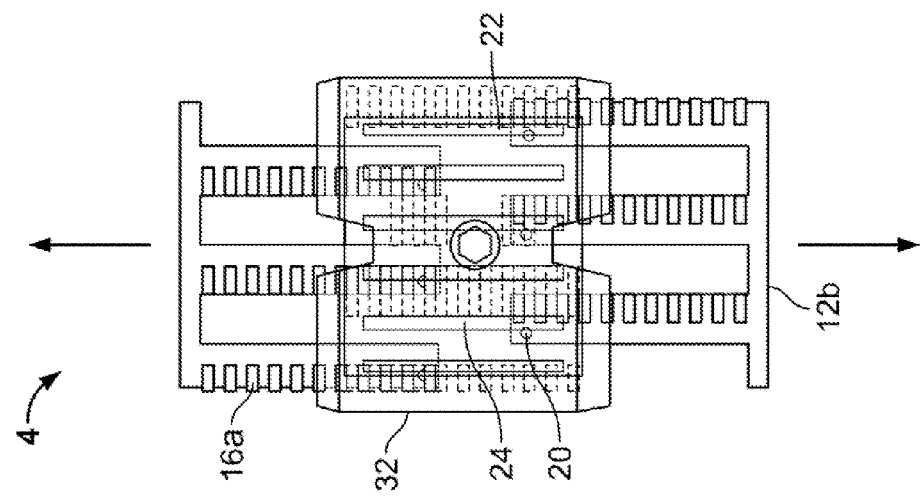
FIG. 7c illustrates a partially constructed partially see-through view of a variation of the device.
Figure 7B:
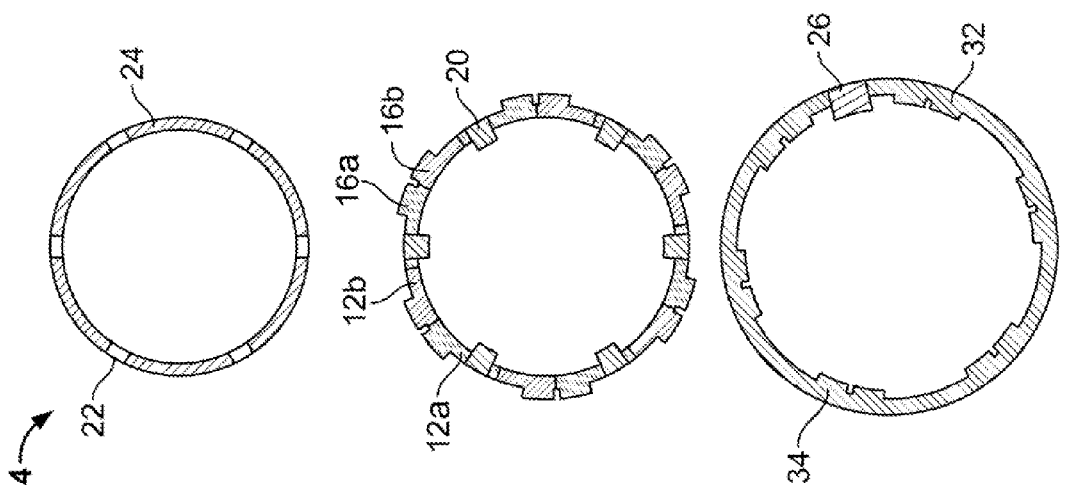
FIG. 7b is a top view of a variation of the partially disassembled components of the device.
Figure 7A:
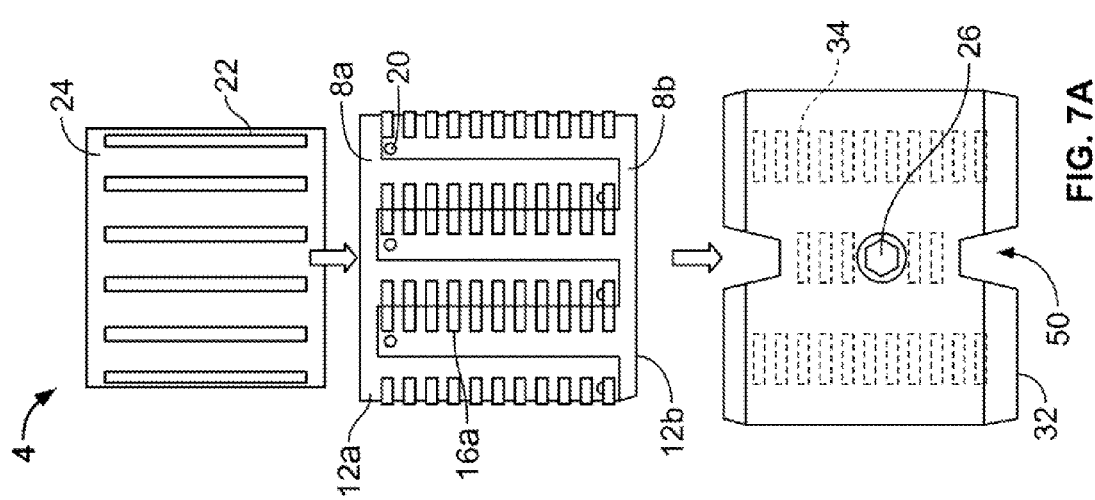
FIG. 7a is an exploded view of a variation of the device.

FIGS. 7a through 7c illustrate a variation of the components of the device similar to those shown in FIGS. 1-6. The outer cylinder teeth 34 can interference fit against the first 16a and second 16b end piece teeth when the device is in a longitudinally locked configuration.

The outer cylinder 32 can have a lock screw 26, such as a hex screw. The lock screw 26 can traverse the wall of the outer cylinder 32. The lock screw 26 can be configured to be radially translatable with respect to the outer cylinder 32 when screwed through the outer cylinder 32 wall. The lock screw 26 can be screwed toward the longitudinal center of the outer cylinder 32 to fix the outer cylinder 32 to the first end piece 12a, second end piece 12b, inner cylinder 24 or combinations thereof, for example, for additional locking.

For example, the lock screw 26 can be tightened (e.g., screwed toward the center of the outer cylinder 32) to press the lock screw 26 against the first 12a and/or second 12b end piece and/or inner cylinder 24 to produce a frictional resistance. The lock screw 26 can deform the first end piece 12a and/or second end piece 12b, pressing the first 12a and/or second 12b end pieces (e.g., the respective extensions) into the inner cylinder 24, creating a frictional force between the inner cylinder 24 and the first 12a and/or second 12b end pieces 12b.

FIG. 7a illustrates that the outer cylinder 32 can have one or more outer cylinder notches 50 along the top and/or bottom of the outer cylinder 32. For example, the notches can be aligned directly adjacent with the lock screw 26 (as shown). The notches can be used to orient or visualize the device during use. Deployment tools can interface with the notches, for example to hold, move or rotate the outer cylinder 32.

FIG. 7c illustrates that when the lock screw 26 can be unscrewed away from the longitudinal center of the outer cylinder 32, releasing the first end piece 12a and second end piece 12b from being fixed to the outer cylinder 32. The first end piece 12a and/or second end piece 12b can be longitudinally translated or extended away from the outer cylinder 32. The guide pegs 20 can slide within the guide slots 22, restricting the end pieces from rotating with respect to the inner cylinder 24.

When the first end piece 12a and the second end piece 12b are translated with respect to the outer cylinder 32 to desired locations, the lock screw 26 can be tightened against the first 12a and/or second 12b end pieces to fix the end pieces to the outer cylinder 32 and prevent or minimize extension or contraction of the device. The lock screw 26 can be unscrewed to compress and reposition or remove the device from the target site 68.

Figure 8C:
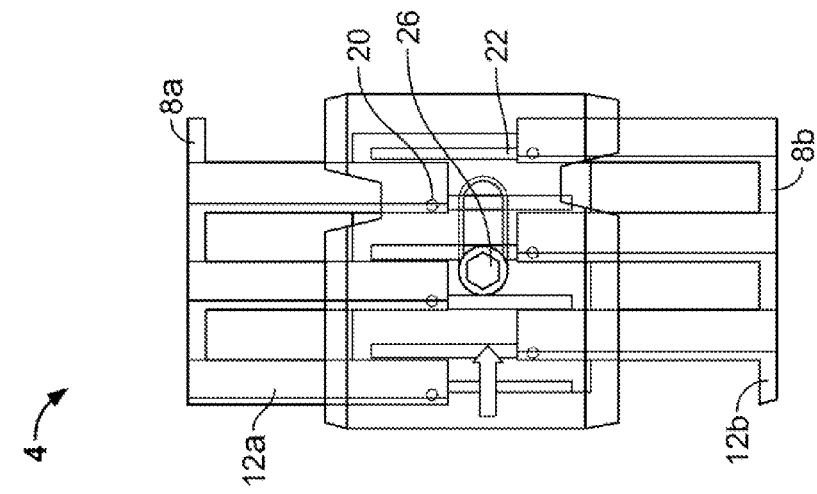
FIG. 8c illustrates a partially constructed partially see-through view of a variation of the device.
Figure 8B:
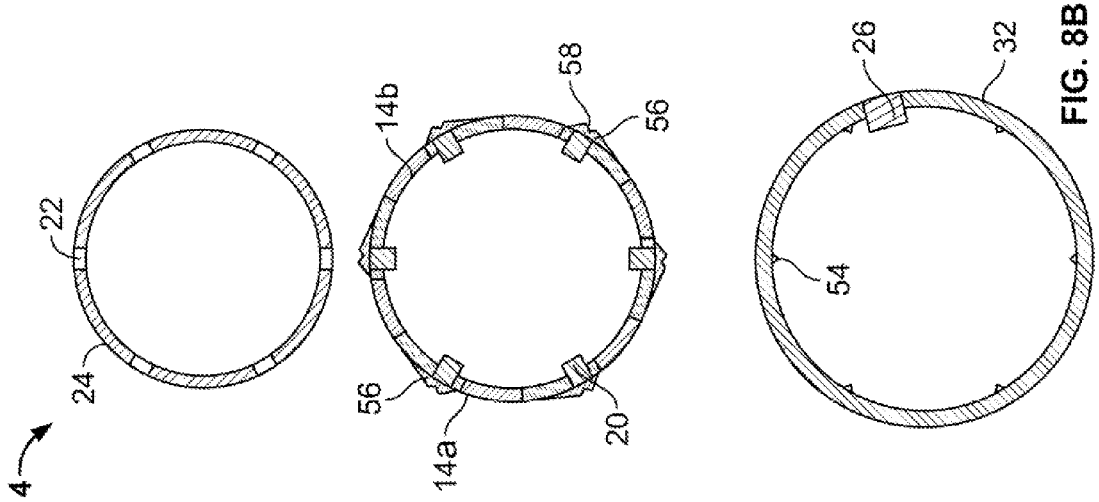
FIG. 8b is a top view of a variation of the partially disassembled components of the device.
Figure 8A:
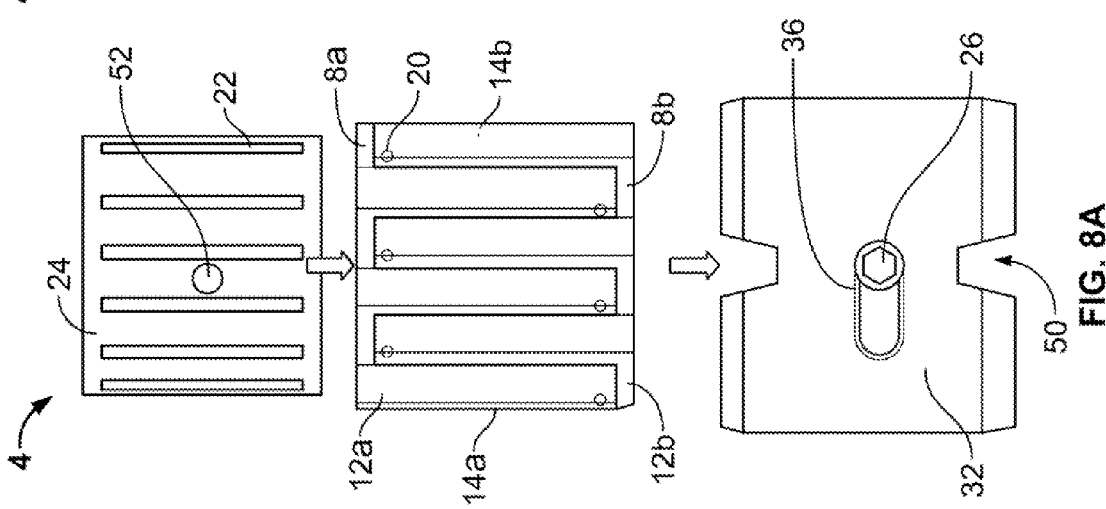
FIG. 8a is an exploded view of a variation of the device.

FIG. 8a illustrates that the outer cylinder 32 or sleeve can have two outer cylinder notches 50 each directly opposed around the screw slot 36. The inner cylinder 24 can have a lock screw port 52. The lock screw 26 can be inserted into the lock screw port 52. The lock screw 26 can be fixed to the inner cylinder 24 or helically rotatably attached to the inner cylinder 24. The inner cylinder 24 can have a textured or otherwise high-friction outer surface.

FIG. 8b illustrates that the outer cylinder 32 can have bumps, wedges, rails or followers 54 extending radially inwardly from the inner wall of the outer cylinder 32. The first end piece extensions 14a and/or the second end piece extensions 14b can have ramps 56 extending radially outwardly from the end piece extensions. The ramps 56 can have ramp seats 58 or divots in the middle of the span of the ramps 56. The first end piece 12a and/or the second end piece 12b, for example along the first end piece extensions 14a and/or the second end piece extensions 14b, can have a textured or otherwise high friction surface along the radially inner-facing surface.

FIG. 8c illustrates that when the outer cylinder 32 is rotated to a locked position, as shown by arrow, with respect to the first end piece 12a and the second end piece 12b, the ramps 56 can slide along the followers 54 and be forced radially inward by the followers 54. The followers 54 of the outer cylinder 32 can press against, and inwardly resiliently or elastically bend or plastically deform, the first end piece extensions 14a and/or second end piece extensions 14b. The end piece extensions having the ramps 56 can then be friction fit between the followers 54 and the inner cylinder 24, resulting in a longitudinally locked configuration for the device. For example, the high-friction, radially inward facing surface of the first and second end pieces 12b can be compressed against and friction fit against the high-friction radially outward facing surface of the inner cylinder 24. The lock screw 26 can then be tightened into the inner cylinder 24, compressing the outer cylinder 32 and the first 12a and second 12b end pieces between the radially outer head of the lock screw 26 and the inner cylinder 24. The followers 54 can reside in the ramp seats 58 when the device is in a locked configuration. The device can have a Morse taper lock as shown.

The devices can have about four, five or six extensions for each end piece, for example. The columns of end piece teeth on adjacent end piece extensions can be directly next to (e.g., with no substantial gap) each other or can be positioned in the center of each extension. When the column of end piece teeth is in the center of each extension, the outer cylinder 32 or sleeve can be turned ½ the distance to lock the device compared to when the column of end piece teeth is directly next to the adjacent column of teeth. The total perimeter of end piece teeth to end piece extension radially outer surface area, or outer cylinder teeth 34 to outer cylinder 32 radially inner surface area can be from about 25% to about 75%, for example about 50%. The area of the radially inner surface of the outer cylinder 32 without, teeth and the area of the radially outer surface of the end pieces can allow the two end pieces to slide relative to each other and to the outer cylinder 32 and can have a smooth or otherwise low or substantially non-friction surface (e.g., coated with PTFE, for example Teflon).

Any or all elements of the expandable support devices 44, and/or deployment tool, and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Any or all elements of the expandable support devices 44, and/or deployment tool, and/or other devices or apparatuses described herein, can be, have, and/or be completely or partially coated with agents and/or a matrix a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, Del.), poly ester amide (PEA), polypropylene, PTFE, ePTFE, nylon, extruded collagen, silicone, any other material disclosed herein, or combinations thereof.

The expandable support devices 44 and/or deployment tool, and/or elements of the expandable support devices 44, and/or deployment tool, and/or other devices or apparatuses described herein and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and *Chlamydia Pneumoniae, Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

Methods of Use

Figure 9B:
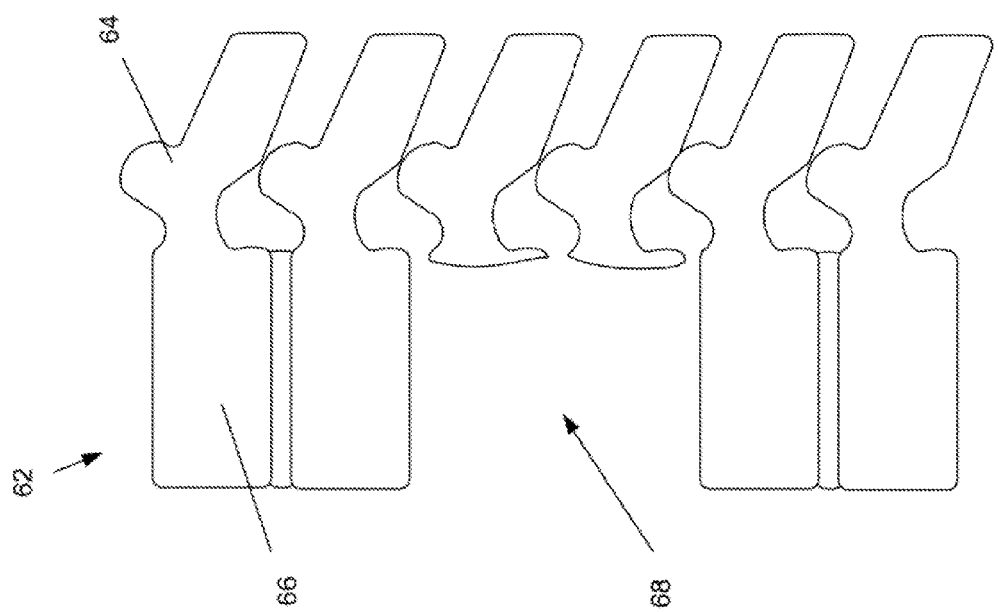
FIG. 9b illustrates a lateral view of the spine of FIG. 9a with a corpectomy.
Figure 9A:
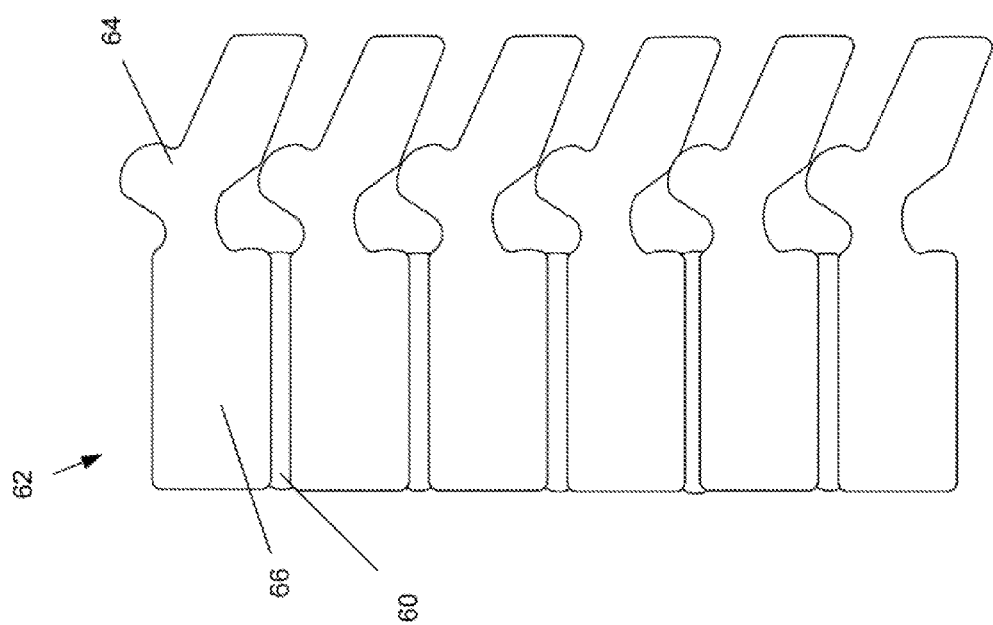
FIG. 9a illustrates a lateral view of a spine.

FIG. 9a illustrates a spine 62 having vertebrae 64 and intervertebral discs 60. One, two or more adjacent vertebral bodies 66 can be pathological, such as having compression fractures necessitating removal of at least the vertebral bodies 66. FIG. 9b illustrates the spine 62 of FIG. 9a, but with two adjacent vertebral bodies 66 and part or all of the adjacent intervertebral discs 60 removed. All or part of the vertebra 64 and surrounding intervertebral discs 60 can be removed. For example, the vertebral body 66 can be removed (i.e., a corpectomy). The empty volume from the removal of tissue can form the target site 68.

Figure 9D:
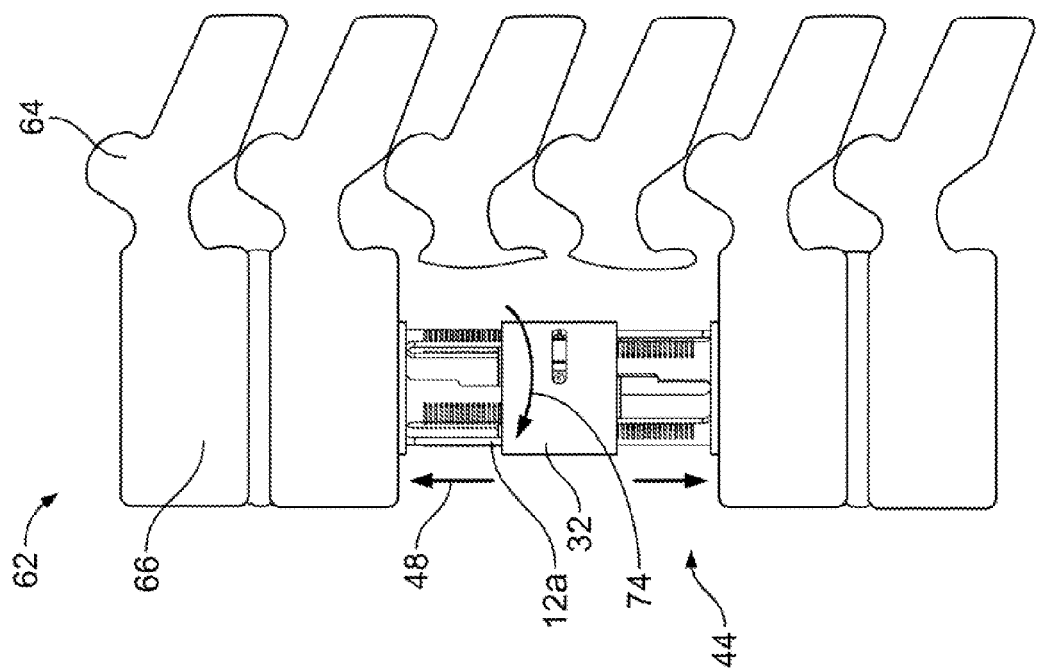
FIGS. 9c and 9d illustrate a variation of a method of using the device in the spine of FIG. 9b.
Figure 9C:
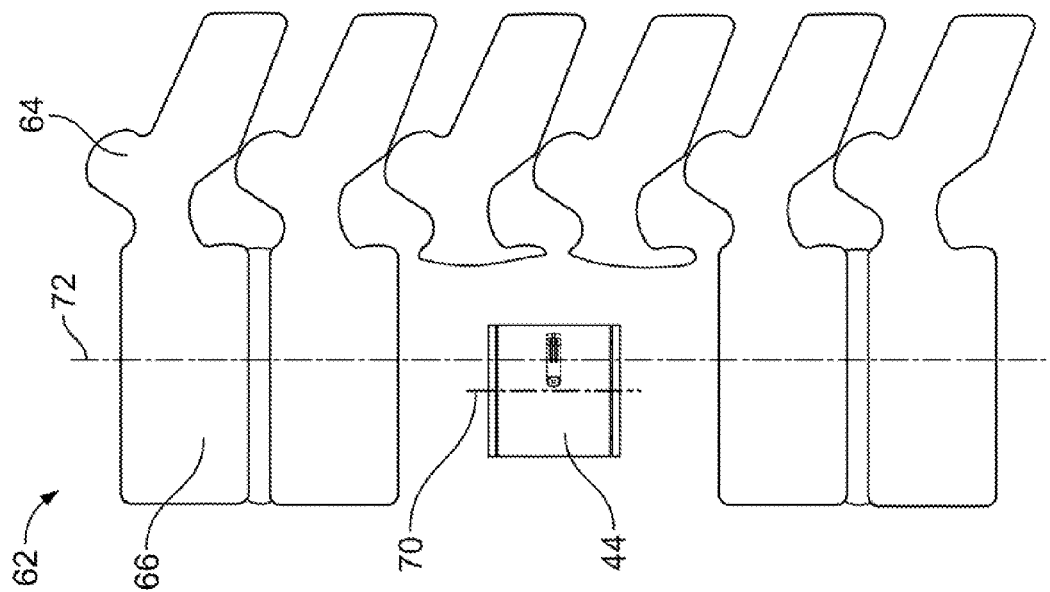

FIG. 9c illustrates that the expandable support device 44 can be in a longitudinally compressed configuration. The expandable support device 44 can be inserted into the target site 68 in the longitudinally compressed configuration or in a longitudinally expanded configuration (e.g., by wedging the expandable support device 44 into the target site 68 and compressing the expandable support device 44 between the remaining vertebral bodies 66 adjacent the target site 68 during insertion). The device longitudinal axis 70 of the expandable support device 44 can be substantially parallel with the spinal longitudinal axis 72.

FIG. 9d illustrates that the expandable support device 44 can be longitudinally expanded 48 in the target site 68. During expansion, the outer cylinder 32 can be in a rotated position with respect to the inner cylinder 24 and the first 12a and second 12b end pieces so the first 16a and second 16b end piece teeth are aligned into the locking gap 28 and slide unobstructed through the outer cylinder 32, in turn allowing the first 12a and second 12b end pieces to slide longitudinally away from the inner 24 and outer 32 cylinders.

The guide pegs 20 can slide longitudinally along the guide slots 22. The guide slots 22 can prevent the guide pegs 20 and the first 12a and second 12b end pieces from rotating with respect to the inner cylinder 24. The guide slots 22 can interference fit when the guide pegs 20 reach the extent of the guide slots 22. The guide slots 22 can limit longitudinal travel of the guide pegs 20, preventing the first 12a and second 12b end pieces from separating from the inner 24 and/or outer 32 cylinders.

When the device is expanded, the device first end 8a and the device second end 8b can be in contact the respective vertebral bodies 66 adjacent to the target site 68. The first 10s and second 10b end faces can be in surface contact with the vertebral bodies 66 or dig or sink into the vertebra 64, for example compressing or diverting some cortical bone. For example, anchors on the first 10a and/or second 10b end faces can be sharp and protrude into the vertebrae 64. The first 10a and/or second 10b end faces can have an ingrowth matrix, anchoring the device to new bone growth through the ingrowth matrix after deployment of the device.

The outer cylinder 32 can be rotated, as shown by arrow 74, with respect to the inner cylinder 24 and end pieces, transforming the device into a locked configuration. The rotated outer cylinder 32 can lock the device in a longitudinally expanded configuration. For example, in the locked configuration, the outer cylinder teeth 34 can form an interference fit with the first end piece teeth 16a and the second end piece teeth 16b. The rotation of the outer cylinder 32 shown in FIG. 9d can be reversed to unlock the device, for example for repositioning or removal.

Expansion of the expandable support device 44 can result in more than about 50% increase in length of the expandable support device 44, or more than about a 100% increase in length, or more narrowly, more than about 125% increase in length, for example about 140% increase in length or about a 145% increase in length between the longitudinally contracted and the longitudinally expanded configuration.

The device can be implanted in the spine 62 for partial or complete corpectomy.

The device can be partially or substantially completely filled with a filler through the slots between the end piece extensions and/or through the ports formed at the longitudinal ends of the device. The device can be filled by the filler before and/or after deployment into the target site 68.

A physician can adjust the length of the device after inspecting the target site 68. More than one device can be placed longitudinal end-to-end with other devices, for example to stack the devices as desired.

The expandable support device 44 can be deployed in a vessel, in or around an aneurysm, across a valve, or combinations thereof. The expandable support device 44 can be deployed permanently and/or used as a removable tool to expand or clear a lumen and/or repair valve leaflets.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. An orthopedic mechanical support device having a longitudinal axis comprising:
a first hollow member having a slot through the first hollow member, wherein the slot is defined by a first stop at a first terminal end of the slot and a second stop at the second terminal end of the slot;
a second hollow member positioned radially inside of the first hollow member, the second hollow member configured to rotate with respect to the first hollow member;
a rotationally limiting element radially extending from the second hollow member, wherein the rotationally limiting element is received by the slot, and wherein the rotationally limiting element and slot are configured to abut at the first stop to limit rotation of the second hollow member with respect to the first hollow member in a first direction, and wherein the rotationally limiting element and the slot are configured to abut at the second stop to limit the rotation of the second hollow member with respect to the second hollow member in the second direction; and
a first longitudinally extending member configured to longitudinally slide with respect to the first hollow member in a first direction away from the first hollow member when the first hollow member is in a first rotational position with respect to the first longitudinally extending member, and wherein the first longitudinally extending member is configured to be longitudinally fixed with respect to the first hollow member when the first hollow member is in a second rotational position with respect to the first longitudinally extending member, and wherein the first longitudinally extending member is configured to be longitudinally slidable along and rotationally fixed to the second hollow member.

2. The device of claim 1, further comprising a second longitudinally extending member configured to longitudinally slide with respect to the first hollow member in a second direction away from the first hollow member when the first hollow member is in a first rotational position with respect to the second longitudinally extending member, and wherein the second direction away from the first hollow member is opposite to the first direction away from the first hollow member, and wherein the second longitudinally extending member is configured to be longitudinally fixed with respect to the first hollow member when the first hollow member is in the second rotational position with respect to the second longitudinally extending member.

3. The device of claim 1, wherein the first longitudinally extending member comprises a first end face, a first extension longitudinally extending from the first end face, and a second extension longitudinally extending from the first end face, wherein a first gap is formed between the first extension and the second extension.

4. The device of claim 3, further comprising a second longitudinally extending member comprising a second end face, a third extension longitudinally extending from the second end face, and a fourth extension longitudinally extending from the second end face, wherein a second gap is formed between the third extension and the fourth extension, and wherein the first extension in configured to longitudinally slide within the first gap and wherein the third extension is configured to longitudinally slide within the second gap.

5. The device of claim 3, wherein the second hollow member comprises a longitudinal guide, and wherein the first extension comprises a guide interface configured to interface with the guide, and be longitudinally slidable along the guide, and be rotationally fixed with respect to the guide.

6. The device of claim 1, wherein the first longitudinally extending member comprises a radially outwardly extending locking feature, and wherein the first hollow member comprises a radially inwardly extending locking feature, and wherein the outwardly extending locking feature interference fits against the inwardly extending locking feature when the first hollow member is in the second rotational position with respect to the second hollow member.

7. The device of claim 1, wherein the slot is in a plane perpendicular to the longitudinal axis.

8. The device of claim 1, wherein the first hollow member and the second hollow member are substantially cylindrical.

9. The device of claim 1, wherein the first end face is hollow.

10. An orthopedic mechanical support device having a longitudinal axis comprising:
   a first hollow member comprising an inner diameter wall and a first hollow member locking feature, wherein the first hollow member locking feature radially inwardly extends from the inner diameter wall;
   a second hollow member radially inside of the first hollow member, wherein the second hollow member is rotatable with respect to the first hollow member, and wherein the second hollow member has a first guide and a second guide;
   a first longitudinally extending member comprising a first radially outwardly extending locking feature and a first radially inwardly extending guide interface; and
   a second longitudinally extending member comprising a second radially outwardly extending locking feature and a second radially inwardly extending guide interface; and
   wherein the first guide interface interfaces with the first guide to limit the rotation between the second hollow member and the first longitudinally extending member, and wherein the first guide interface interfaces with the first guide to allow and limit longitudinal movement between the second hollow member and the first longitudinally extending member; and
   wherein the second guide interface interfaces with the second guide to limit the rotation between the second hollow member and the second longitudinally extending member, and wherein the second guide interface interfaces with the second guide to allow and limit longitudinal movement between the second hollow member and the second longitudinally extending member.

11. The device of claim 10, wherein the first hollow member comprises a second hollow member locking feature, and wherein a locking gap is defined between the first hollow member locking feature and the second hollow member locking feature.

12. The device of claim 11, wherein the width of the first radially outwardly extending locking feature and width of the second radially outwardly extending locking feature are together less than or equal to the width of the locking gap.

13. The device of claim 12, wherein the widths of the first radially outwardly extending locking feature and the second radially outwardly extending locking feature are each less than the width of the hollow member locking feature.

14. The device of claim 10, wherein a rotationally limiting element extends from the second hollow member through the first hollow member, and wherein the rotation of the first hollow member with respect to the first longitudinally extending member and the second longitudinally extending member is limited by the rotationally limiting element interference fitting against the first hollow member.

15. A method for mechanically supporting an orthopedic site comprising:
   inserting a longitudinally expandable device into the orthopedic site, wherein a support device has a longitudinal axis and comprises a first hollow member, a second hollow member radially inside of the first hollow member, and a first longitudinally extending member slidably received by the first hollow member;
   longitudinally extending the first longitudinally extending member from the first hollow member; and
   longitudinally fixing the first longitudinally extending member to the first hollow member, wherein longitudinally fixing comprises rotating the first hollow member with respect to the first longitudinally extending member;
   wherein the support device further comprises a second longitudinally extending member slidably received by the second hollow member, and wherein the method further comprises longitudinally extending the second longitudinally extending member from the first hollow member in a direction opposite to a direction of the extension of the first longitudinally extending member.

16. The method of claim 15, wherein rotating the first hollow member comprises rotating the first hollow member until the first hollow member interference fits against a feature of the second hollow member.

17. The method of claim 15, wherein longitudinally extending the first longitudinally extending member comprises longitudinally sliding a guide interface on the first longitudinally extending member along a guide on the second hollow member.

18. The method of claim 15, further comprising rotationally restricting the first longitudinally extending member with respect to the second hollow member.

19. The method of claim 15, further comprising removing a vertebral body from the orthopedic site before inserting the expandable device into the orthopedic site.

\* \* \* \* \*